United States Patent [19]

Cullick

[11] Patent Number: 4,672,840
[45] Date of Patent: Jun. 16, 1987

[54] METHOD AND SYSTEM FOR DETERMINING FLUID VOLUMES OF A TWO-PHASE EFFLUENT FLUID FLOW THROUGH A POROUS MATERIAL

[75] Inventor: Alvin S. Cullick, Dallas, Tex.

[73] Assignee: Mobil Oil Corporation, New York, N.Y.

[21] Appl. No.: 797,097

[22] Filed: Nov. 12, 1985

[51] Int. Cl.$^4$ ............................................. G01N 15/08
[52] U.S. Cl. ........................................ 73/38; 73/61 R
[58] Field of Search ................... 73/38, 73, 153, 149, 73/304 C; 324/61 R

[56] References Cited

U.S. PATENT DOCUMENTS

| | | | |
|---|---|---|---|
| 2,445,494 | 7/1948 | Redmond | 73/153 |
| 3,523,245 | 8/1970 | Love et al. | 324/61 R |
| 4,023,096 | 5/1977 | Schmidt | 324/61 R |
| 4,070,903 | 1/1978 | Lees | 73/38 |
| 4,304,122 | 12/1981 | Tentor | 73/38 |
| 4,381,665 | 5/1983 | Levine et al. | 73/73 |
| 4,444,051 | 4/1984 | Yamaki et al. | 73/304 C |
| 4,487,056 | 12/1984 | Wiley | 73/38 |
| 4,531,404 | 7/1985 | Phelps et al. | 73/38 |
| 4,543,821 | 10/1985 | Davis, Jr. | 73/38 |

FOREIGN PATENT DOCUMENTS 1125511 11/1984 U.S.S.R. ........................ 73/38

Primary Examiner—Stewart J. Levy
Assistant Examiner—Hezron E. Williams
Attorney, Agent, or Firm—Alexander J. McKillop; Michael G. Gilman; George W. Hager, Jr.

[57] ABSTRACT

A liquid hydrocarbon and an insoluble displacing fluid are passed through a core sample from a subsurface formation. The two-phase effluent flow out of the core sample is collected in a container where the two phases separate into an overlying fluid phase and an underlying fluid phase and the volumes of each phase are measured as an indication of the permeability of the core sample. Such volumes are measured by placing fluid level detectors in the container and detecting the movements of the air-fluid interface of the top of the overlying fluid phase and the fluid-fluid interface between the two phases as the fluid is drained from the container.

9 Claims, 1 Drawing Figure

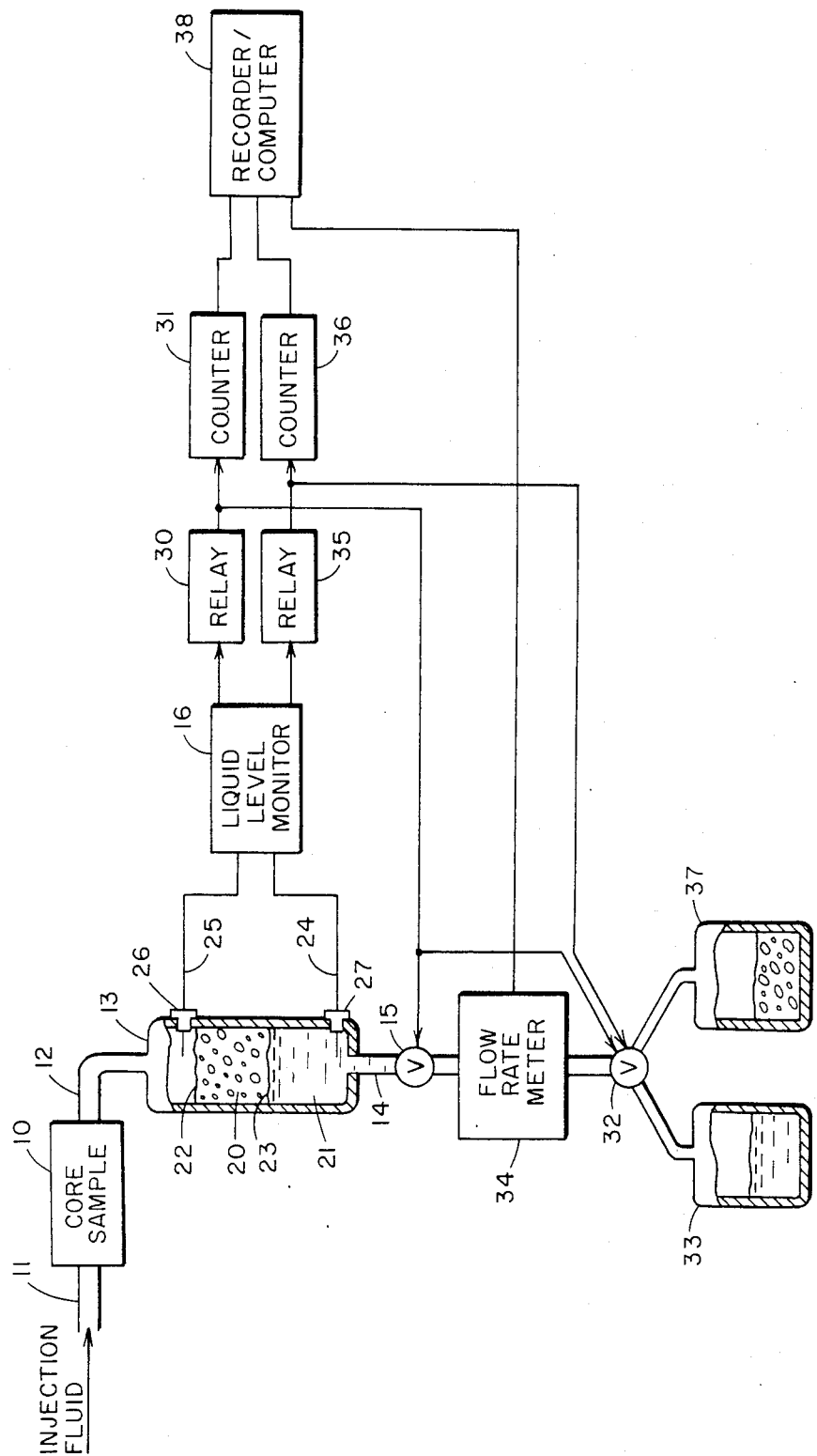

METHOD AND SYSTEM FOR DETERMINING FLUID VOLUMES OF A TWO-PHASE EFFLUENT FLUID FLOW THROUGH A POROUS MATERIAL

BACKGROUND OF THE INVENTION

This invention relates to a method and system for determining certain characteristics of porous material taken from subsurface formations and, more particularly, to a method and system for determining permeability of a core sample taken from a subsurface hydrocarbon-bearing reservoir by measuring the fluid volumes of a two-phase effluent fluid flow through the core sample.

In the production of an oil or gas reservoir, it is important to know certain lithological properties of the reservoir. One of the most important of these properties is the permeability of the reservoir rock in which the oil or gas is stored. Permeability is a measure of the ability of the reservoir rock to transmit fluids through pore spaces in the porous rock material and is inversely proportional to the flow resistance offered by the material. A core sample of a subsurface rock material is generally tested for permeability by forcing a fluid through the core sample, which has been previously saturated with the same fluid, and measuring the rate of flow of the fluid through the core sample.

SUMMARY OF THE INVENTION

The present invention is directed to a new method and system for determining fluid volumes of a two-phase effluent fluid flow through a porous material so that the permeability characteristic of the porous material may be determined. A two-phase fluid flow condition is established through the porous material, such as a core sample taken from a subsurface hydrocarbon-bearing reservoir. One phase is a liquid hydrocarbon phase, and the other phase is an insoluble displacing liquid phase. After exiting the core sample, the two-phase fluid is collected in a container where it separates into an overlying fluid phase (e.g., oil) and an underlying fluid phase (e.g., water). A fluid level monitor is positioned in the container. When the air-fluid interface of the top of the overlying fluid phase rises to a first position in the upper portion of the container, drainage of the underlying fluid phase from the container is initiated. The time is measured during which the fluid-fluid interface between the overlying and underlying fluid phases is lowered to a second position near the bottom of the container. The time is also measured during which the air-water interface of the top of the overlying fluid phase is lowered to the same second position near the bottom of the container. The volumes of each of the two fluid phases are determinable from the two time measurements and the drainage flow rate of the fluid, such volumes being representative of the fluid saturation in the core sample, from which core sample permeability is determined.

In a further aspect of the invention, changes in capacitance between such first and second positions within the container are used to identify the locations of the two fluid phases. This capacitance is measured between electrical conductors at such first and second positions with the changing of the air-fluid and fluid-fluid interfaces acting as a changing dielectric between the electrical conductors.

In another aspect of the invention, changes in fluid density between such first and second positions with the container are used to identify the locations of the two fluid phases. Such density changes are measured by fluid density cells located at such first and second positions.

BRIEF DESCRIPTION OF THE DRAWING

The drawing illustrates a system for carrying out the fluid volume determination of a two-phase effluent fluid flow through a porous material of the present invention.

DESCRIPTION OF THE PREFERRED EMBODIMENT

Referring now to the drawing, there is disclosed a system for carrying out the method of the present invention. A core sample 10 of a porous material is taken from a subsurface formation. This core sample is initially saturated with a liquid hydrocarbon, such as oil; an insoluble displacing fluid, such as water; or brine; or a combination thereof. Thereafter, a two-phase effluent fluid flow is established through the core sample by the continuous injection of oil, water, or a combination thereof into the core sample through channel 11. This two-phase effluent fluid flow out of core sample 10 is carried by way of channel 12 into the upper portion of a fluid container 13. A drainage channel 14 leads from the lower portion of container 13. This drainage channel is initially closed by the valve 15. As the two-phase effluent fluid is collected in the container 13, it separates into an overlying liquid hydrocarbon phase (i.e., oil) and an underlying insoluble displacing fluid phase (i.e., water) 21. As such fluid is collected and later drained therefrom as described hereinbelow, a liquid level monitor 16 continually detects the position within the container 13 of both the air-fluid interface 22 at the top of the overlying oil phase and the fluid-fluid interface 23 between the overlying oil phase and the underlying water phase.

In one embodiment of the invention, liquid level monitor 16 measures the capacitance between a pair of electrodes 24 and 25 which pass through the container by means of feed through terminals 26 and 27, respectively, and are located at spaced-apart vertical positions within the container 13. The lower electrode 24 needs to be located near the bottom of the container 13 so that an accurate determination can be made of the completion of the drainage on the two fluid phases. The underlying and overlying fluid phases 21 and 20, respectively, along with the air space above overlying fluid phase 20 form the dielectric between the two electrodes 24 and 25 in a capacitance-type liquid level measuring system.

With the valve 15 in a closed position, the two-phase effluent flow from core sample 10 begins to fill the container 13, the two phases separating in the process. When the air-fluid interface at the top of the overlying fluid phase rises so as to make contact with electrode 25, a distinct capacitance change is noted across the electrodes 24 and 25. This new capacitance is converted into a proportional voltage signal by the liquid level monitor 16 for use in the activation of a relay 30. In turn, relay 30 activates a counter 31 and opens valve 15 to initiate drainage of the underlying fluid phase 21 from container 13. Relay 30 also operates valve 32 to cause the drainage of the underlying fluid phase to be collected in the container 33. The flow rate meter 34 detects the rate at which such underlying fluid phase is drained from container 13.

As the fluid level in container 13 lowers, the fluid-fluid interface 23 contacts electrode 24 near the bottom of container 13. A capacitance change is again detected by the liquid level monitor 16, thereby indicating that the underlying fluid phase 21 has been drained from container 13. At this time, the liquid level monitor 16 activates relay 35. In turn, relay 35 activates counter 36 and changes the position of valve 32 to initiate drainage of the overlying fluid phase into container 37. Also at this time, counter 31 may continue to run along with counter 36, or it may be inactivated by liquid level monitor 16 and relay 30. Should counter 31 be inactivated, the recorded count will represent the time required for the underlying fluid phase to be drained from container 13. Should counter 31 not be inactivated at this time, it will continue to run, along with counter 36, until the air-fluid interface 22 of the top of the overlying fluid phase makes contact with electrode 24. At this time, liquid level monitor 16 again detects a change in capacitance across electrodes 24 and 25. In turn, liquid level monitor 16 inactivates counter 36 and, likewise, counter 31 if it had not been inactivated earlier in time as described above. Also, valve 15 is closed and valve 32 is returned to its original position. The recorded count in counter 36 represents the time required for the overlying fluid phase 20 to be drained from container 13. If counter 31 had not been inactivated earlier, it now represents the time for both fluid phases to be drained from the container 13. Accordingly, the difference in the counts of counter 31 and 36 represent the time for the underlying fluid phase 21 to be drained from container 13.

In a yet further alternative, both counters 31 and 36 may be activated by the air-fluid interface 22 reaching the electrode 25, counter 31 may be inactivated when the fluid-fluid interface 23 reaches electrode 25, and counter 36 may be inactivated when the air-fluid interface 22 reaches electrode 24. In this alternative, the count in counter 31 represents the time for drainage of the underlying fluid phase 21, while the difference in the counts of the counters 31 and 36 represent the time for drainage of the overlying fluid phase 20.

Upon completion of the drainage process of both phases of the fluid in container 13, and the closure of valve 15 and switching of valve 32, the refilling and subsequent drainage of container 13 can be repeated as needed so long as the drainage flow rate of the fluid out of container 13 significantly exceeds the effluent flow rate of the fluid out of core sample 10. Typical core effluent flow rate is in the range of 5 to 100 cubic centimeters per hour. Typical drainage rate from container 13 is greater than 100 cubic centimeters per minute.

In carrying out the above-described method, a particularly suitable flow cell assembly for holding core sample 10 so as to allow the two-phase effluent flow is shown in detail in U.S. Pat. No. 4,531,404 to Phelps and Sampath, the contents of which are incorporated herein by reference. Another suitable flow cell assembly reference is U.S. Pat. No. 2,345,935 to Hassler. A suitable capacitance-type liquid level monitor 16 includes a capacitance-to-frequency converter and a frequency-to-voltage converter, such as shown in detail in U.S. Pat. No. 4,381,665 to Levine and Marek, the contents of which are also incorporated herein by reference. As an alternative to the capacitance-type liquid level monitor, one of several conventional liquid level detecting devices might be utilized including a device, such as the densimeter cell, for detecting fluid density changes as the various fluid interfaces pass the location of the density cell. One such densimeter cell is the Mettler/Paar DMA 512. A suitable flow rate meter 34 is the Rheotherm meter supplied by Intek, Inc. or the Omniflo meter supplied by Flow Technology, Inc.

While a particular embodiment of the present invention has been shown and described, other modifications may be within the true scope and spirit of the invention. The appended claims are, therefore, intended to cover such modifications.

I claim:

1. A method for determining fluid volumes of a two-phase effluent fluid flow through a porous material, comprising the steps of:
    (a) establishing a two-phase fluid flow condition through said proous material, one phase being a liquid hydrocarbon and the other phase being an insoluble displacing liquid,
    (b) collecting said two-phase fluid in a container as it passes from said porous material, said two-phase fluid separating in said container into an overlying fluid phase and an underlying fluid phase so that there is an air-fluid interface at the top of said overlying fluid phase and a fluid-fluid interface between said underlying and overlying fluid phases,
    (c) positioning a fluid level monitor in said container,
    (d) initiating fluid drainage from the lower portion of said container when the air-fluid interface of the top of the overlying fluid phase rises to a first position in the upper portion of said container, the flow rate of said fluid drainage from said container being greater than the flow rate of said fluid into said container,
    (e) determining a first time required for the fluid-fluid interface between said underlying and overlying fluid phases to lower to a second position near the bottom of said container,
    (f) determining a second time required for the air-fluid interface of the top of the overlying fluid phase to lower to said second position near the bottom of said container,
    (g) determining the flow rate of said fluid drainage from said container, and
    (h) determining the volumes of each of the two phases of said fluid from said first and second time determinations and said flow rate determination, said volumes being representative of the saturation of said porous material.

2. The method of claim 1 including the steps of:
    (a) detecting a first change in capacitance between said first and second positions within said container caused by the rising of the air-fluid interface of the overlying fluid phase to said first position for use in initiating the fluid drainage from said container,
    (b) detecting a second change in capacitance between said first and second positions within said container caused by the lowering of the fluid-fluid interface between the overlying and underlying fluid phases to said second position for use in making said first time determination, and
    (c) detecting a third change in capacitance between said first and second positions within said container caused by the lowering of the air-fluid interface of the top of the overlying fluid phase to said second position for use in making said second time determination.

3. The method of claim 2 wherein the steps of detecting changes in capacitance between said first and second positions within said container are carried out by utilizing the changing of the air-fluid and fluid-fluid interfaces between said first and second positions as a changing dielectric between electrical conductors at said first and second positions.

4. The method of claim 1 including the steps of:
  (a) detecting a first change in the medium density at said first position within said container caused by the rising of the air-fluid interface of the top of the overlying fluid phase to said first position for use in initiating the fluid drainage from said container,
  (b) detecting a second change in the medium density at said second position within said container caused by the lowering of the fluid-fluid interface between the overlying and underlying fluid phases to said second position for use in making said first time determination, and
  (c) detecting a third change in the medium density at said second position within said container caused by the lowering of the air-fluid interface of the top of the overlying fluid phase to said second position for use in making said second time determination.

5. The method of claim 1 further including the steps of:
  (a) initially directing the drainage of said fluid from said container through a first channel when the air-fluid interface of the top of the overlying fluid phase rises to said first position in said container, and
  (b) redirecting the drainage of said fluid from said container through a second channel when the fluid-fluid interface between the underlying and overlying fluid phases lowers to said second position in said container, whereby fluid separation is effected between said underlying and overlying fluid phases.

6. A method for measuring fluid volume in a two-phase effluent flow stream from a displacement test of a core sample from a subsurface formation, comprising the steps of:
  (a) taking a core sample from a subsurface formation suspected of being oil-bearing,
  (b) saturating said core sample with water, oil, or some combination thereof,
  (c) passing a flooding fluid through said core sample, said flooding fluid being water, oil, or some combination thereof,
  (d) collecting the two-phase, water-oil effluent flow from said core sample in a container,
  (e) allowing said two-phase effluent fluid to separate in said container with a distinguishable fluid interface being formed between an underlying water phase and an overlying oil phase,
  (f) initiating drainage of said fluid from said container when the top of the oil phase rises to a first fixed level in said container,
  (g) measuring the time required for both said water phase and said oil phase to be drained from said container, and
  (h) determining the fluid volumes of said oil and water phases from said measured times and the rate of fluid drainage from said container.

7. A system for measuring fluid volume in a two-phase effluent flow stream, comprising:
  (a) a fluid container,
  (b) a first fluid level detector positioned to detect fluid interfaces within an upper portion of said container,
  (c) a second fluid level positioned to detect fluid interfaces in a lower portion of said container,
  (d) a first opening in said container for flowing said two-phase fluid into said container,
  (e) a second opening for draining said two-phase fluid from said container,
  (f) valve means for controlling the drainage of said two-phase fluid through said second opening,
  (g) means for closing valve means, to allow said two-phase fluid to accumulate in said container, said fluid separating into underlying and overlying fluid phases, with a distinguishable fluid interface being formed between said first and second fluid level detectors,
  (h) at least two counters,
  (i) means for controlling said counters in response to said fluid level detectors so as to measure the drainage time of at least two of the following from said container:
    (i) uderlying fluid phase,
    (ii) overlying fluid phase, or
    (iii) both said underlying and overlying fluid phases,
  (j) means for measuring the flow rate of said two-phase fluid from said container, and
  (k) means for determining the volumes of each phase of said two-phase fluid from said measured drainage times and drainage flow rate.

8. The system of claim 7 wherein said first and second fluid level detectors measure a fluid density.

9. The system of claim 7 wherein said first and second fluid level detectors measure the capacitance of the medium between said detectors, changes in said measured capacitance identifying changes in the fluid content at one of said fluid level detectors.

* * * * *